United States Patent
Anatolievich

[11] Patent Number: 5,666,971
[45] Date of Patent: Sep. 16, 1997

[54] DEVICE FOR IMPROVING ERECTION

[76] Inventor: Pomozov Pyotr Anatolievich, ul. Kavkazski Bulevard 35 kv. 329, 115516 Moscow, Russian Federation

[21] Appl. No.: 140,446

[22] Filed: Oct. 25, 1993

[51] Int. Cl.⁶ .................................................. A61F 6/02
[52] U.S. Cl. .......................... 128/842; 128/844; 128/918
[58] Field of Search ................................ 128/842, 844, 128/918; 604/330, 347–353

[56] References Cited

U.S. PATENT DOCUMENTS

| | | | |
|---|---|---|---|
| 1,225,341 | 5/1917 | Lederer | 600/38 |
| 4,074,712 | 2/1978 | Wright | 600/39 |
| 4,381,000 | 4/1983 | Duncan | 600/39 |
| 4,872,447 | 10/1989 | Tsirjulnikov | 600/39 |
| 5,111,831 | 5/1992 | Foggia | 128/844 |
| 5,121,755 | 6/1992 | Hogedusch | 128/844 |
| 5,158,556 | 10/1992 | Starley | 128/844 |
| 5,199,444 | 4/1993 | Wheeler | 128/844 |

FOREIGN PATENT DOCUMENTS 9100076   1/1991   WIPO ................................ 128/918

*Primary Examiner*—Michael A. Brown
*Attorney, Agent, or Firm*—Ilya Zborovsky

[57] ABSTRACT

A device for improving erection, having a ring-shaped base having two walls spaced from one another to define a cavity therebetween, a cylindrical elastic closed cover connected to the base and having a portion which is arcuate-shaped and adapted to cover the head of the penis. A longitudinal portion which is adapted to cover the shaft of the penis. The arcuate portion having a thickness of 0.1–2.00 mm.

3 Claims, 2 Drawing Sheets

DEVICE FOR IMPROVING ERECTION

BACKGROUND OF THE INVENTION

The present invention relates generally to devices for improving erection.

Erection improving devices are known and utilized with many modifications. Some devices have a stiff rod with a ring at its end. Such devices are disclosed, for example in U.S. Pat. Nos. 4,785,802, 4,643,175, 4,842,447. However, these devices are not sufficiently effective and non-ethical.

Devices of a different type include a cover which is put on the penis and connected with a source of vacuum. Due to the negative pressure under the cover, a blood influx to the penis and its passive erection is provided. Such devices are disclosed, for example in U.S. Pat. Nos. 4,671,262, 4,384,527, 4,641,638, 4,753,227. Such devices are however bulky, since they are connected with the vacuum pump. As a result, the user experiences a discomfort, which affects the physiological process of sexual intercourse.

Another erection improving device or an erector is formed as a hard or semi-hard cover with characteristics which are close to the characteristics of a penis prosthesis. This device mainly produces friction; however, the user does not experience the normal sensibility of the penis head. Also, there is no passive erection due to the absence of the zone with a negative pressure. Such devices are disclosed, for example in U.S. Pat. Nos. 3,397,689 and 4,640,270.

It is to be understood that further improvements of the existing devices, in particular of the device disclosed in U.S. Pat. No. 3,397,689, are desirable.

SUMMARY OF THE INVENTION

Accordingly, it is an object of the present invention to provide a device for improving erection, which is a further improvement of the existing devices of this type and is superior to the latter.

In keeping with these objects and with others which will become apparent hereinafter, one feature of the present invention resides, briefly stated, in a device for improving erection, which has a ring-shaped body with two walls spaced from one another to define a cavity therebetween; and a cylindrical elastic closed cover connected with said base and having a portion which is arcuate-shaped and adapted to cover the head of the penis and a longitudinal portion which is adapted to cover the shaft of the penis, the arcuate-shaped portion having a thickness of 0.1–2.00 mm, a longitudinal portion having a wall thickness which is determined as follows:

$S_x = S_o + K_x L_x$ wherein $S_x$ is a wall thickness of the portion of the longitudinal portion;

$S_o$ is a wall thickness of the arcuate-shaped portion;

$L_x$ is a length of the portion of the cylindrical cover from the arcuate portion of the cylindrical cover to a given rear portion of the cylindrical portion; and K is a coefficient of a material hardness equal to substantially 0.01–0.03.

When the device is designed in accordance with the present invention, it eliminates the disadvantages of the prior art and provides for highly advantageous results.

The novel features of the present invention are set forth in particular in the appended claims. The invention itself, however, will be best understood from the following description of preferred embodiments, which is accompanied by the following drawings.

DESCRIPTION OF THE PREFERRED EMBODIMENTS

Figure 1:
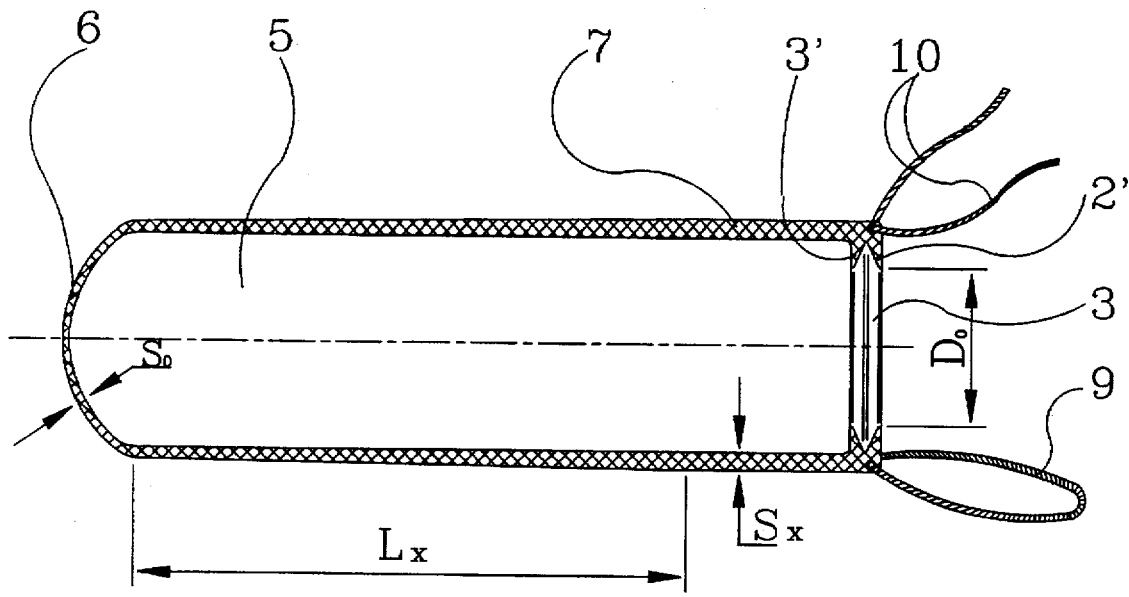
FIG. 1 is a view showing a longitudinal section of a device for improving erection in accordance with the present invention.
Figure 2:
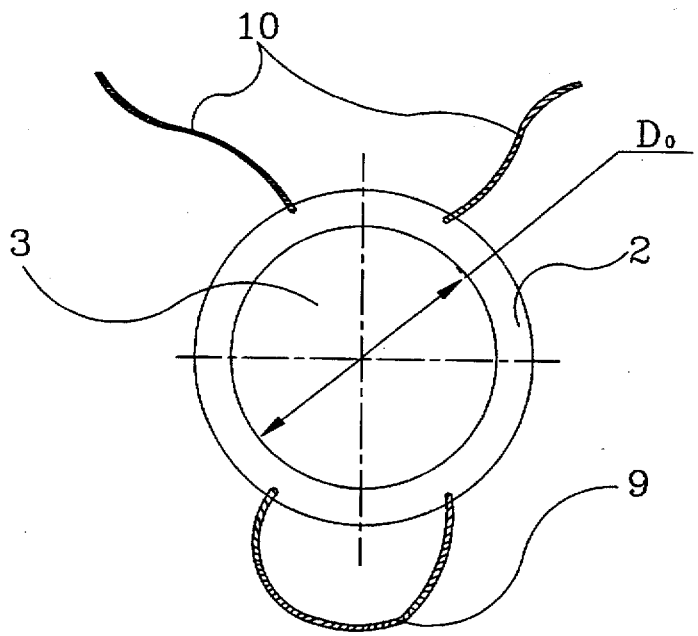
FIG. 2 is a view showing the inventive device for improving erection, as seen from the side of its base part.

FIG. 1, shows the longitudinal section of the device as set forth below in detail and FIG. 2, shows the rear end view of device as set forth in detail below.

A device for improving erection in accordance with the present invention has a ring-shaped base 1 with two walls 2 and 3, spaced from one another to define a cavity 4 therebetween. The device further has a cylindrical elastic closed cover 5 connected with the base 1 and having a portion 6 which is arcuate-shaped and adapted to cover the head of the penis. The arcuate-shaped portion 6 has a thickness of 0.1–2.00 mm. The cover 5 further has a longitudinal portion 7 with a wall thickness which is determined as follows:

$S_x = S_o + K_x L_x$ wherein $S_x$ is a wall thickness of the portion of the longitudinal portion;

$S_o$ is a wall thickness of the arcuate-shaped portion;

$L_x$ is a length of the portion of the cylindrical cover from the arcuate portion of the cylindrical cover to a given rear portion of the cylindrical portion; and K is a coefficient of a material hardness equal to substantially 0.01–0.03.

The device further has a means for fixing. The fixing means includes a loop 9 and cord portions 10 as illustrated in FIG. 1.

The device for improving erection in accordance with the present invention operates in the following manner:

First, the device is adjusted in accordance with a prospective user as follows. The length of the device is selected in accordance with a desire of partners or anatomical length of penis during its full erection, The diameter of an opening in the base of the device is equal to the diameter of penis in non-erected condition. The wall thickness of the arcuate portion is selected such that the tactile sensibility while touching the outer side of the wall is maintained. It has been established that this wall thickness is within the range of 0.1–2.0 mm.

Before use the device is warmed up by introducing it in water with the temperature of 50°–60° for 20–30 minutes. Then the cavity 4 is filled with a lubricating material, for example vaseline. The outer surface of the device is lubricated as well. Then the device is compressed so as to remove air from its interior, the head of the user's penis is introduced into an opening 8 of the base, and then unclench the hand and "draw" the penis into the device. The device must envelope the penis, however without any painful sensations. The thusly produced compression effect prevents blood outflow from the penis and improves its filling with blood, which is of a special importance for the process. In order to fix the device to a user, then the rubber cord is fixed at the base of the user's scrotum, and the cord ends are tied at the back and the device is firmly held on the user's body.

The preservation of the normal sensibility of the penis head during the frictions due to the correctly selected wall leads to strengthening of the erection, while the hardness of the cylindrical part provides a proper sexual intercourse even when the erection is insufficient. The hermeticity of the device and the removal of air from it produces a zone of a reduced pressure which leads to the increase of the blood filling of the penis. Thus, the device in accordance with the present invention combined three factors which lead to the improvement of erection and which have not been used in their interaction and interjunction in any of the known erection improving devices.

The specific design of the device in accordance with the present invention is illustrated by the following examples.

EXAMPLE 1

A patient was 50 years old, suffering from impotence. It has been determined during the selection of the device that the tactile sensibility is maintained with the wall thickness of the portion which imitates the penis head 0.5 mm, and the length of this portion 20 mm. The length of the device selected in accordance with anatomical characterstics of the patient was 160 mm. The diameter of the opening in the base was 32 mm. The wall thickness of the cylindrical cover in the remaining portion was determined in accordance with the above presented formula. The wall thickness at the distance of 100 mm from the closed end was 1.3 mm.

The device is composed of a polymeric material which is harmless for human organism and has elasticity and color corresponding to those of the human penis. For example the polymeric material can have the following composition:

| | |
|---|---|
| PVC emulsion, EP 66020 TU 6-01-5743-67-96-88 | 41.8% |
| PVC M64794 TU 6-01-678-86 | 10.5% |
| Dioktylphtalat (DOF) GOST 8278-77 | 43.4% |
| Epoxidated oil (Soybean oil) TU 6-10-722-86 | 3.13% |
| Oleic Acid TU 6-09-5290-86 | 0.02% |
| Ridamin "P" (10% alcoholic solution) TU 6-09-2463-82 | 1.05% |
| Titanium white GOST 9808-84 | |

Figure 3:
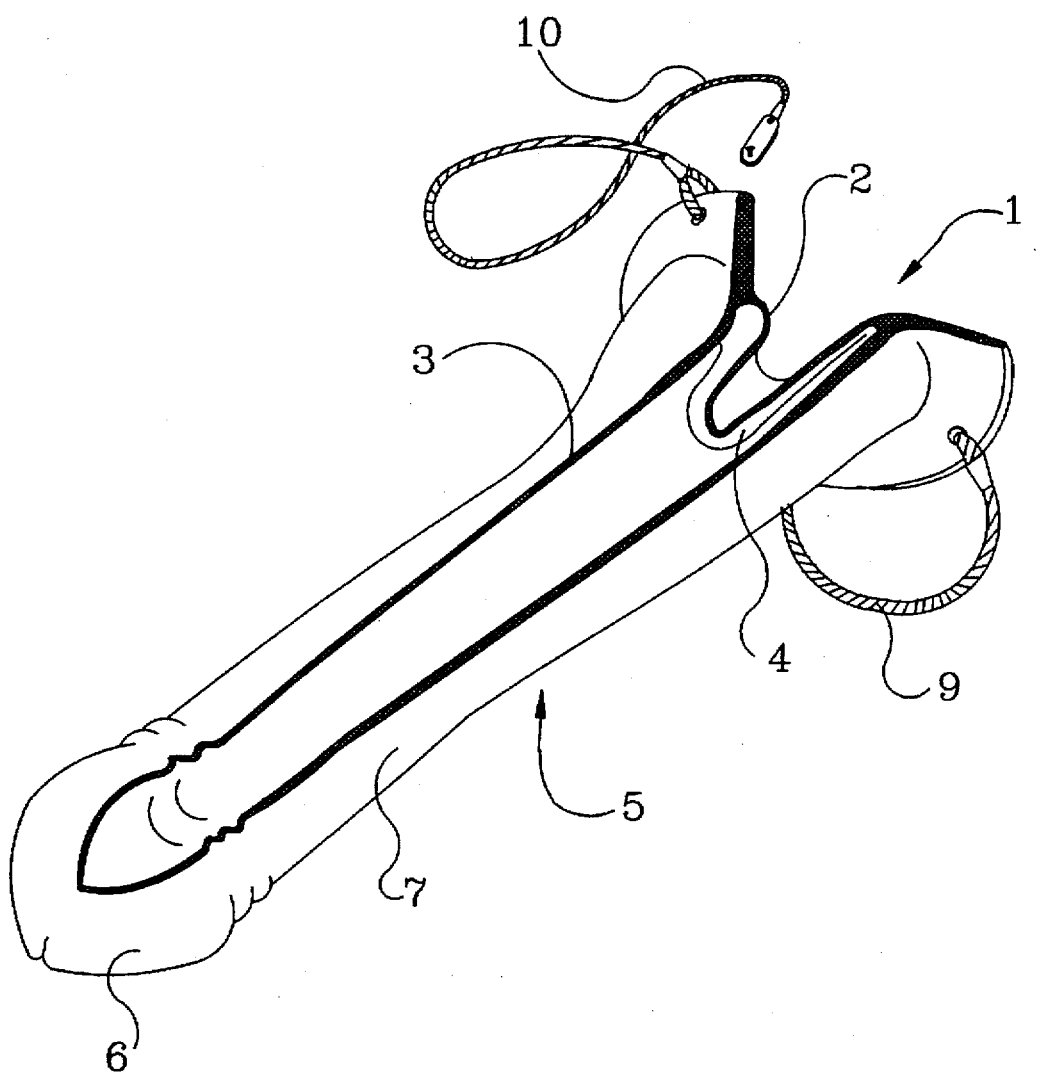
FIG. 3 is a general view of the device for improving erection, formed in accordance with the present invention.

FIG. 3 shows a modification for patients which do not have a penis due to surgical procedure or have only a short part of it. In contrast, FIG. 1 shows a modification for men with a penis which can be inserted into the device. Here the rear rings 2' and 3' extend not parallel to the axis of the device as in FIG. 3, but instead perpendicular to the axis. When the penis is inserted, the rings 2' and 3' are compressed, air is expelled from the cavity between them, and the thusly produced suction increases the hold of the device on the penis.

It is the main feature of the invention that the penis body imitating portion is thicker and thereby harder, while the penis head imitating portion is thinner and thereby softer. The formula in the specification makes possible an accurate determination of the thickness of the penis body imitating portion.

The above described features provide for exceptionally efficient use of the device and natural sexual intercourse when the device is utilized, which is almost the same as a natural sexual intercourse with a man having normal penis and normal erections.

It will be understood that each of the elements described above, or two or more together, may also find a useful application in other types of devices' differing from the types described above.

While the invention has been illustrated and described as embodied in a device for improving erection, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. A device for improving erection, comprising a ring-shaped base having two walls spaced from one another to define a cavity therebetween;

a cylindrical elastic closed cover connected with said base and having a portion which is arcuate-shaped and adapted to cover the head of the penis and a longitudinal portion which is adapted to cover the shaft of the penis, said arcuate-shaped portion having a thickness of 0.1–2.00 mm, said longitudinal portion having a wall thickness which is determined as follows:

$S_x = S_o + k \cdot L_x$, wherein $S_x$ is a wall thickness of the portion of the longitudinal portion;

$S_o$ is a wall thickness of the arcuate-shaped portion $L_x$ is a length of the portion of the cylindrical cover from the arcuate portion of the cylindrical cover from the arcuate portion to a given rear portion of the cylindrical portion;

K is a coefficient of a material hardness equal to substantially 0.01–0.03.

2. A device for improving erection as defined in claim 1, further comprising a means for fixing the device to a patient.

3. A device for improving erection as defined in claim 2, wherein said means for fixing the device includes a loop that is a rubber cord. The device further has a means for fixing. The fixing means includes a loop 9 and cord portions 10 as illustrated in FIG. 1.

* * * * *